United States Patent [19]

Rait

[11] Patent Number: 5,429,611
[45] Date of Patent: Jul. 4, 1995

[54] SYRINGE WITH AUTOMATICALLY ACTUATED SHIELD

[76] Inventor: Joseph M. Rait, 1100 Amherst St., Buffalo, N.Y. 14080

[21] Appl. No.: 74,396

[22] Filed: Jun. 10, 1993

[51] Int. Cl.⁶ ............................................. A61M 5/32
[52] U.S. Cl. .................................. 604/197; 604/110; 604/195; 604/198
[58] Field of Search ............... 604/197, 264, 198, 187, 604/192, 199, 110, 263, 195, 231–232, 221–222; 433/90

[56] References Cited

U.S. PATENT DOCUMENTS

| | | | |
|---|---|---|---|
| 3,019,790 | 2/1962 | Militana | 606/108 |
| 4,631,057 | 12/1986 | Mitchell | 604/198 |
| 5,104,386 | 4/1992 | Alzain | 604/232 |
| 5,273,541 | 12/1993 | Malenchek | 604/110 |
| 5,292,314 | 3/1994 | D'Alessio et al. | 604/198 |
| 5,306,258 | 4/1994 | de la Fuente | 604/198 |

*Primary Examiner*—C. Fred Rosenbaum
*Assistant Examiner*—V. Alexander
*Attorney, Agent, or Firm*—Howard M. Cohn

[57] ABSTRACT

An inner tubular assembly positioned in telescoping arrangement with an outer tubular protective assembly forms a chamber for a fluid receptacle in a hypodermic syringe; it supports a hypodermic needle and a piston plunger to inject fluid from or draw fluid into the receptacle. Biasing means acting between the inner and outer assemblies urge the inner assembly including the outer end of the needle to a retracted position. Levers in the form of finger pieces are pivotally mounted on the outer assembly; the levers are biased to urge the lugs formed at their ends through apertures in the outer assembly and into engagement with a shoulder at the lower end of the inner assembly to latch it in retracted position. When the finger pieces are grasped to use the syringe the latch is actuated to released position. Other lugs at the upper portion of the finger pieces aaaare engageable with a shoulder on the upper portion of the inner tubular assembly to retain the needle in exposed position ready for injection.

17 Claims, 2 Drawing Sheets

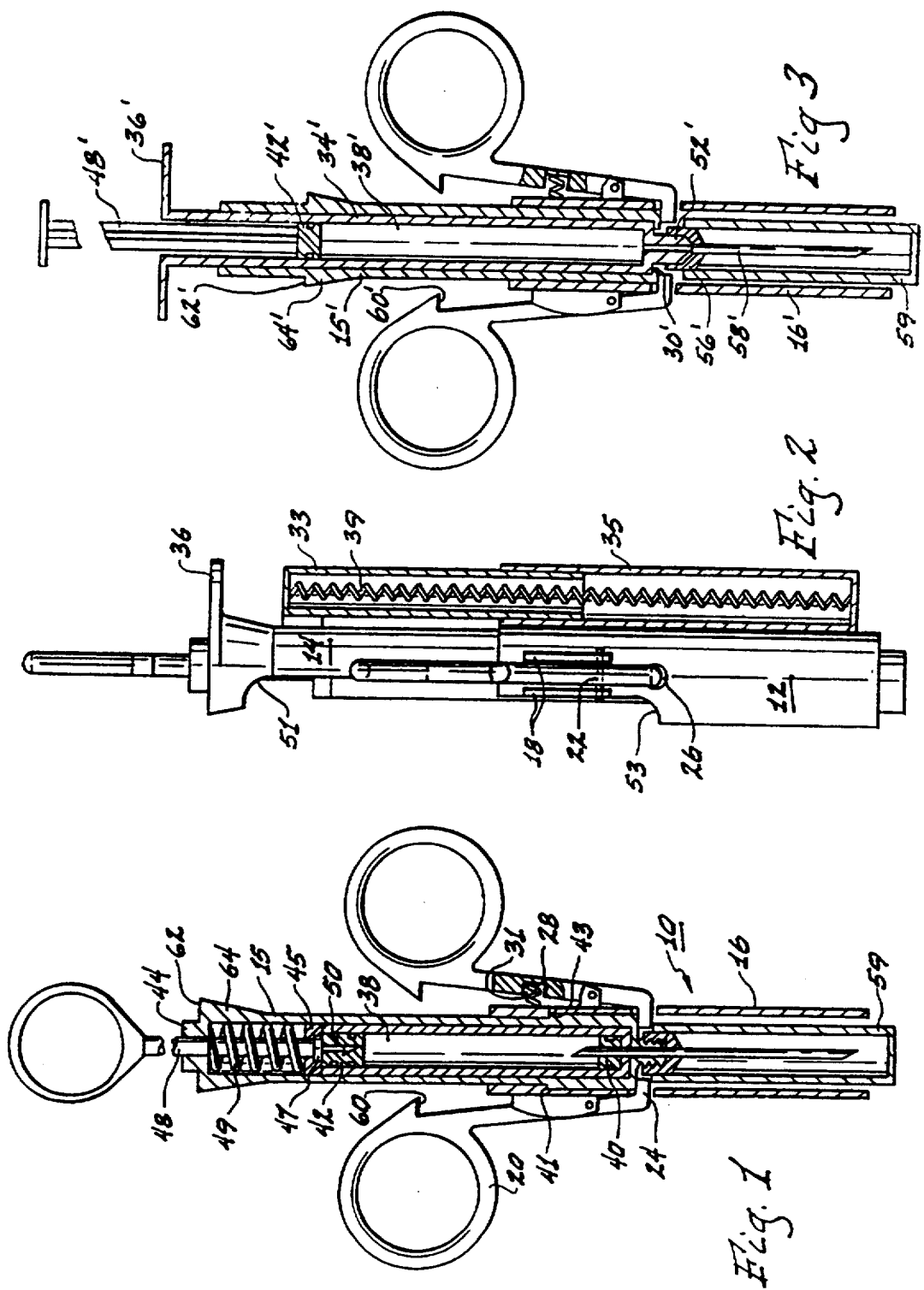

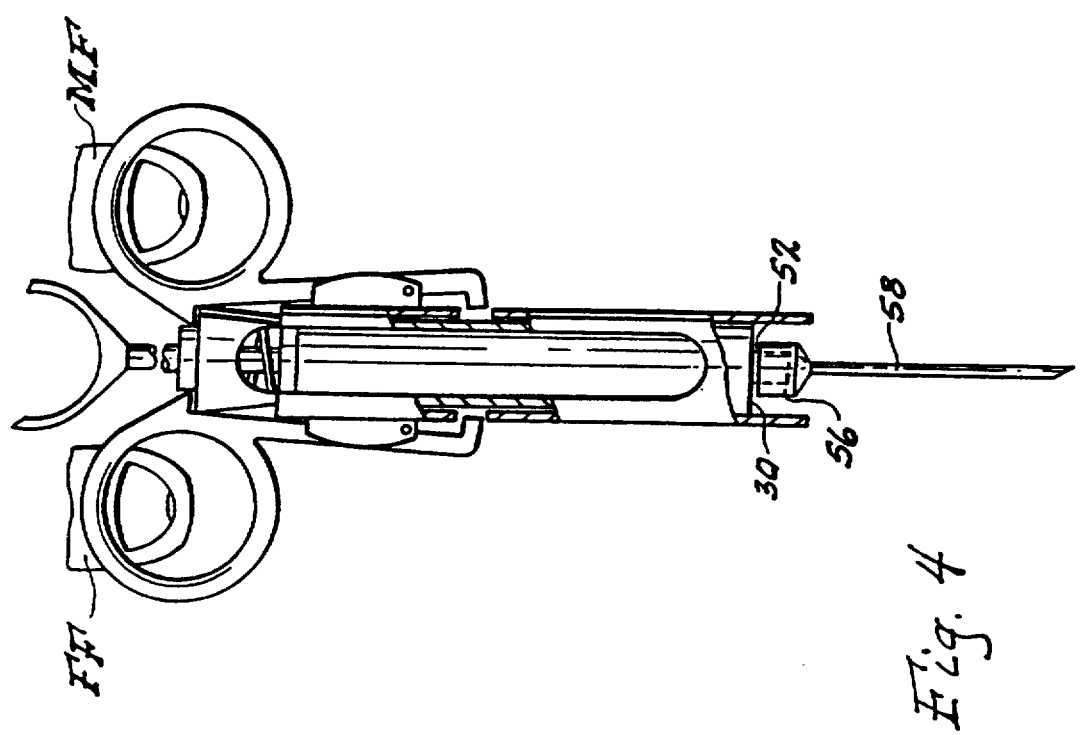

SYRINGE WITH AUTOMATICALLY ACTUATED SHIELD

BACKGROUND OF THE INVENTION

1. Field of the Invention

The invention relates to hypodermic syringes and, more particularly, to a protective enclosure assembly in which the hypodermic needle is automatically, positively but releasably retained in a retracted position.

2. Prior Art

Needle protectors are well known and have been in use for many years for needles used with hypodermic syringes. Conventionally, needles are made with hubs and sockets adapted to be attached to the reduced end of a syringe. A molded plastic cap is removably secured to the hub of the needle. After mounting the needle on the syringe, the cap is removed to expose the needle for use. Following use the protective cap is replaced to prevent needle sticks during disposal.

Accidental needle stick injuries are extremely common among nurses, physicians, laboratory workers, dentists and other health care workers. Such injuries frequently occur during recapping of a needle after use or when a syringe is left on a work surface with needle exposed.

Transmission of hepatitis, the acquired immune deficiency syndrome (AIDS) and other contagious diseases can result from inadvertent needle sticks with contaminated needles.

A plethora of prior art discloses diverse needle protective devices which replace or supplement the conventional sheath with resilient devices which are biased or hand manipulated to enclose the needle following its use. Springs, bellows and inherently resilient material are employed to provide the biasing force. Examples are the following U.S. Pats.:

White No. 2,876,770 Mar 10, 1959 Spring biased

Vaillancourt No. 4,725,267 Feb. 16, 1988 Bellows/manual

Schwartz No. 4,775,369 Oct. 4, 1988 Inherent resiliency

All of the above mentioned projective shields are relatively complex additions to the conventional shield and are discarded along with the disposable needles. Such devices are expensive. They also can interfere with the view of the area to be injected and none are positively retained in the needle shielding position. All of the known prior art automatically actuated shields are of flexible material which may permit inadvertent contact with the needle.

SUMMARY OF THE INVENTION

The syringe protective enclosure assembly of this invention comprises a pair of tubular assemblies disposed in telescoping relationship. The inner tubular member or assembly serves as a chamber for a disposable hypodermic syringe assembly or for a carpule, plunger and disposable needle of suitable length and size. The needle may be enclosed by the conventional removable and replaceable sheath. When the parts are positioned for use, a substantial portion of the needle is exposed for insertion into a patient. However, the entire outer assembly is normally biased to and retained in an extended position relative to the inner member, thus shielding the needle point in an inaccessible position to thereby prevent accidental pricking. A coil spring acting axially between the inner and outer members biases the outer member to the extended position.

Finger pieces are pivotally attached on the outer member and have radially inwardly projecting lugs at their inner ends in alignment with and normally biased to extend through apertures in the outer member. The lugs engage a shoulder at the inner end of the inner member to retain it in retracted position. Near the outer end of each of the finger pieces a second lug is formed. The second lug is engageable with a shoulder on the outer portion of the inner tubular member; when the second lug is engaged with the shoulder the needle is retained in exposed position ready for use. This occurs only when the user positively actuates it to the engaged position.

In use the fore finger and middle finger may be inserted into loops at the outer end of the finger pieces. The finger pieces act as levers and pivot against their normal bias to disengage the inner an outer tubular members. The thumb is placed against a thumb piece extending radially from the outer end of the inner tube; continued pressure on the thumb piece causes the needle to move to an exposed position where it can be injected into a patient; it is retained in this position because the second pair of lugs engage the outer or upper shoulder of the inner tubular member so long as the finger pieces are held by the user. Thereupon fluid cam either be injected or withdrawn depending upon the needs of the patient by actuation of the plunger in the usual manner. After use when the fingers are removed from the loops of the finger pieces the biasing spring courses the needle to retract within the outer tubular member in which position the needle is automatically latched.

The principle object of the present invention is to provide an improved, fail safe, reusable shielding device for a syringe needle point which automatically renders the point inaccessible to fingers or any part of the body while permitting sufficient access to remove and/or replace the conventional molded shield.

Another object of the invention is to provide an improved reusable protective enclosure for use with a hypodermic syringe assembly adaptable to incorporate conventional disposable syringe apparatus wherein the syringe needle point is automatically disposed to and positively retained in a shielded retracted position before and after use.

Other objects and advantages of the invention will be apparent form the following detailed description taken in connection with the accompanying drawings.

BRIEF DESCRIPTION OF THE DRAWINGS

FIG. 1 is a side elevation view of the syringe of this invention with needle and carpule in place in retracted position, partly in section;

FIG. 2 is a partial elevation view axially rotated 90 degrees from FIG. 1 showing the biasing mechanism;

FIG. 3 is a diagrammatic view of a modified embodiment of the inner tubular assembly in retracted position.

FIG. 4 is side elevation similar to FIG. 1 illustrating the syringe with needle extended, plunger depressed and sheath removed; and FIG. 5 is a view similar to FIG. 2 with axial biasing spring compressed and needle extended.

DETAILED DESCRIPTION OF THE INVENTION

Referring to FIG. 1 protective enclosure assembly 10 for use in conjunction with hypodermic syringe apparatus includes an outer tubular protective assembly 12 and an inner tubular assembly 14 arranged telescopically. The outer tubular assembly 12 comprises an outer tubular member 16 having pairs of spaced apart ears 18 fixed at diametrically opposite sides of outer tubular member 16. Each pair of ears 18 pivotally supports a lever serving as one of the finger pieces 20. The finger pieces 20 pivot on an axis formed by pivot pin 22. At their upper ends the finger pieces 20 are shown as circular but may be any suitable or desirable shape to accommodate grasping by the fingers of the user. At their lower ends each is formed with a radially inwardly extending lug 24 serving as engaging means aligned with an aperture 26 formed in the sidewall of outer tubular member 16. Apertures 26 provide for access to engage a lower shoulder 30 serving as first keeper or retaining means at the lower end of inner tubular assembly 14. Above the pivot pin 22 a compression spring 28 is captured between the barrel or sidewall of outer tubular member 16 and a recess 31 formed in finger piece 20. The spring 28 biases the finger piece 20 about axis 22 to urge lugs 24 through apertures 26 into engagement with shoulder 30.

The inner tubular assembly 14 is positioned within the outer tubular assembly 12; it comprises an inner tubular member 15 telescopically slidable within the outer tubular member 16. The walls of the inner and outer tubular members may be cut away as at 51 and 53, respectively to form windows in circumferential alignment. The windows provide for side or lateral insertion of a carpule 38. In accordance with the invention axially extending compression spring housings 33 and 35 are fixed to inner and outer tubular members 15 and 16, respectively. The spring housings 33 and 35 are positioned for telescopic interengagement with each other to form a spring cage for a compression spring 39. The spring cage and enclosed compression spring constitutes biasing means to urge the inner assembly 14 to a retracted position as shown in FIG. 1. An external circumferential flange 41 on inner tubular assembly 14 engages an internal circumferential flange 43 on outer tubular assembly 12 to prevent inadvertent disassembly by action of spring 39. When the outer assembly 12 is disposed in its normally biased extended position as shown in FIG. 1 lugs 24 at the ends of finger pieces 20 are biased by spring 28 to enter apertures 26. The lugs 24 engage a shoulder or keeper 30 adjacent the lower end of the inner tubular member 15 to retain and latch the inner tubular member 15 in retracted position with respect to outer tubular assembly 12.

At its upper end the outer wall surface of the inner tubular member 15 slopes upwardly and outwardly to form shoulder or second keeper 62 and cam surface 64. Extending radially outward from the shoulder 62 is thumb piece 36. On the periphery of each of the finger rings at the side adjacent the walls of the tubular assembly, a second lug 60 is formed to engage upper shoulder 62 adjacent the upper or outer end of the inner tubular member 15. With forefinger FF and middle finger MF in position in the finger rings as illustrated in FIG. 4, thumb pressure on thumb piece 36 will release the lugs 24; inner tubular member and contained needle and carpule will move outwardly to extended position. Second lugs 60 will be cammed upwardly and outwardly and into engagement with shoulder or keeper 62. So long as the fingers FF and MF are in engagement with the finger pieces the needle will be retained in exposed position and can be injected. Shifting the thumb at this point to the top of the plunger and exerting thumb pressure will cause fluid to eject. Upon spreading fingers FF and MF or removing them from the finger pieces the outer protective tubular member 16 will automatically be moved by the biasing spring to the extended position covering needle as seen in FIG. 1.

Inner tubular member 15 provides a chamber for either body fluids or injectable fluids; it may accommodate and support a conventional disposable syringe 38' as illustrated in FIG. 3 or it may be loaded with a carpule 38 as shown in FIG. 1.

The carpule 38 or fluid carrying unit constituting receptacle means is cylindrically shaped, closed at its forward end by a head plug 40 and at its rear end by a piston plug 42. The plugs are preferably of pliant material as for example rubber; both are penetrable by sharpened points. A bearing 44 at the rear end of inner tubular member 14 journals the stem of plunger 48 for axial movement. A penetrating pin 50 having a spurred end is provided at the forward end of the plunger for penetration of piston plug 42; the plunger 48 can drive the piston 42 in either direction to withdraw a body fluid or to inject a fluid. A circumferential collar 47 at the free end of the plunger stem supports a spring guide 45 for axial movement within the inner tubular member 15. A compression spring 49 encircles the plunger stem between spring guide 45 and the undersurface of collar bearing 44. To insert the carpule 38 the plunger is pulled up compressing spring 49; the carpule is inserted through the windows 51 and 53; the plunger is then released driving penetrating pin 50 into the piston 42 at the upper end of the carpule.

At the lower end of inner tubular member 14 may be formed a reduced diameter portion serving as a support 52 for a needle 58 and forming shoulder 30. The needle support 52 may be threaded as shown in FIG. 1 to receive the internally threaded hub 56 of needle 58 as shown. Alternatively the hub 56 may be secured to needle support 52 by a friction fit. It is desirable to provide a protective shield 59 preferably of molded plastic to cover needle 58 while the needle is being affixed or removed for disposal. The shield 59 frictionally engages hub 56.

The needle 58 is one type of conventional needle and may vary to accommodate the various inner tubular member constructions suggested. The needle support 52 may vary to accommodate diverse needle constructions; it may be provided with a central bore for passing the rear portion of needle 58. As shown the rear portion of needle 58 penetrates head plug 40 to establish fluid communication with the carpule. When the inner tubular member 15 is latched in retracted position as shown in FIG. 1, the sharpened outer end of needle 58 is enclosed and shielded by outer tubular member 16 to prevent an accidental needle stick.

The modified embodiment shown in FIG. 3 is constructed to accommodate a conventional disposable plastic syringe assembly 38' which comprises a cylindrical body 34' serving as fluid receptacle means. Parts illustrated in FIG. 3 identified by prime numbers are the same or similar to parts identified by the same basic numbers in FIGS. 1 and 2. The body 34' includes a radially outward extending flange 36' at its rear end (or upper end as illustrated) end which may serve as a thumb piece; a reduced diameter portion 52' at its outer end (or lower end as illustrated) forms a needle support. Hub 56' of needle 58' may be affixed by a friction fit. A plunger 48' is telescopically received in body 34' and axially slidable therein. A piston 42' of elastomeric material is secured to the lower end of plunger 48'. The protective enclosure assembly embodiment illustrated in FIG. 3 differs from the FIG. 1 embodiment in that the free end of the inner member 15' is open to accommodate syringe assembly 38' and in the omission of the thumb piece 36. At its lower or outer end inner tubular assembly 15' includes a radially inwardly extending circumferential flange 30' forming a shoulder which is engageable with lugs 24 in the retracted position and serves as a support for disposable syringe assembly 38'. The flange 30' also forms an opening to receive needle support 52'. Similar to the FIG. 1 embodiment the needle 58' may be enclosed by an identical plastic shield 59 before and after use.

The interior of outer tubular member 16' can be accessed to replace the protective shield 59 after use. The protective shield can be removed prior to use when the needle is extended. It will be apparent that although the shield 59 is accessible, the end of the contaminated needle cannot be inadvertently touched by the user. At this point the needle may be projected and removed for disposal and all other disposable elements can be removed and appropriately discarded.

Similarly, in accordance with the FIG. 3 embodiment, the disposable plastic syringe assembly 38' may be inserted into the chamber of inner tubular assembly 15'. By grasping the finger pieces 20 a above described, placing the thumb on flange 36' and applying force thereto the latch lugs 24 will disengage and the inner tubular assembly together with the syringe will move forwardly to expose the needle. Thereupon the procedure is identical with the procedure of the FIG. 1 embodiment.

It should now be apparent that a unique protective enclosure assembly for use in conjunction with a hypodermic fail safe in that the needle is spring biased to a retracted position and therefore automatically moves to a shielded position. It is also latched in the retracted position by a spring biased latch. Even if carelessly left lying in an unsafe place where it is likely to be inadvertently touched no contaminated needle sticks can result. The inner and outer tubular members may be manufactured from metal or durable plastic so as to be reusable. Although certain specific embodiments and modifications of the invention have been shown and described for purposes of illustration, it will, of course be understood that other and various embodiments are possible within the scope of the invention. For example, certain elements like the inner tubular assembly may be of various materials such as metal plastic or other suitable or desirable materials. The fluid receptacle may take forms different from the those described. The biasing means may vary. For example, the finger pieces could employ leaf springs in lieu of coil springs. Either one or both of the finger pieces could serve as latches. Other and different variations are possible.

Therefore, it should be apparent that the invention is not limited to the specific arrangement shown, but in its broadest aspects includes all equivalent embodiments and modifications which come within the scope of the invention.

What I claim is:

1. A hypodermic syringe adapted to receive a container of fluid, said syringe comprising:
   an outer tubular member;
   an inner tubular member having chamber means, said inner tubular member being in telescopically slidable relationship within said outer tubular member;
   needle support means at a first end of said inner tubular member for attaching a needle assembly;
   plunger means mounted to a second opposite end of said inner tubular member, said plunger means being axially movable within said inner tubular member for causing a flow of fluid through said needle assembly and into or out of said container of fluid;
   resilient means for biasing said outer tubular member to an extended position whereby said needle assembly is enclosed within said outer tubular member;
   latching means on said outer tubular member cooperating with retaining means on said inner tubular member for both securing said outer tubular member in said extended position and for retaining said outer tubular member in a retracted position to expose said needle assembly, said latching means including first lug means for engaging a first keeper adjacent the first end of said inner tubular member and second lug means for engaging the second end of said inner tubular member.

2. The hypodermic syringe of claim 1 wherein said latching means includes lever means with said first lug means at a first end thereof for latching engagement with a first keeper means on said inner tubular member whereby axial movement between said inner and outer tubular members is prevented when said outer tubular member is in said extended position, said lever means further including said second lug means at a second opposite end of said lever means to engage a second keeper on said inner tubular member to retain said outer member in said retracted position whereby said needle assembly is exposed.

3. The hypodermic syringe of claim 2 wherein said latching means includes biasing means to effect said latching engagement between said inner and outer tubular members.

4. The hypodermic syringe of claim 3 wherein said lever means comprises a pair of levers which are pivotally secured to said outer tubular member.

5. The hypodermic syringe of claim 4 wherein said pair of levers have loops at their free ends to serve as finger pieces for grasping said syringe during use.

6. A hypodermic syringe comprising:
   an outer tubular member;
   an inner tubular member having a chamber, said inner tubular member being disposed in telescopically slidable relationship within said outer tubular member;
   needle support means at a first end of said inner tubular member;
   plunger means disposed at a second end of said inner tubular member being adapted for engagement with said container of fluid;
   resilient means for normally biasing said outer tubular member to an extended position whereby when said needle assembly is attached to said inner tubular member said needle assembly is enclosed by said outer tubular member; and
   manually releasable latching means pivotally secured to said outer tubular member, said latching means including lever means with first engaging means at a first end for latching engagement with a first keeper means on said inner tubular member whereby axial movement between said inner and outer tubular members is prevented when said outer tubular member is in said extended position, said latching means further including second engaging means at a second opposite end of said lever means for latching engagement with a second keeper means on said inner tubular member to retain said outer member in a retracted position whereby said needle assembly is exposed.

7. The hypodermic syringe of claim 6 wherein said latching means includes biasing means to effect said latching engagement between said inner and outer tubular members when said outer tubular member is in said extended position.

8. The hypodermic syringe of claim 6 wherein said lever means comprises a pair of levers which are pivotally secured to said outer tubular member.

9. The hypodermic syringe of claim 8 wherein said pair of levers each include a loop at their free ends to serve as finger pieces for grasping said syringe during use.

10. The hypodermic syringe of claim 9 wherein said pair of levers are diametrically oppositely disposed on said outer tubular member.

11. The hypodermic syringe of claim 6 wherever said first engaging means includes a first lug means at a first end of said inner tubular lever means for latching engagement with said first keeper means on said member.

12. The hypodermic syringe of claim 11 wherein said second keeper means includes a cam surface on said inner tubular member sloping outwardly toward said second end to form a circumferential shoulder and said second engaging means includes a lug extending inwardly from said lever means, said lever means being positioned in operative engagement with said cam surface and engageable with said shoulder to retain said needle assembly in an exposed position while manual pressure is applied to said levers means.

13. The hypodermic syringe of claim 6 wherein said inner and outer tubular assemblies have aligned cut away portions through their sidewalls.

14. The hypodermic syringe of claim 6 wherein said inner tubular member is open at its second end for reception of said container of fluid.

15. The hypodermic syringe of claim 14 wherein said container of fluid is a disposable hypodermic syringe insertable into the inner tubular member through said open end.

16. A hypodermic syringe adapted to receive a container of fluid, said syringe comprising:
   an outer tubular member;
   an inner tubular member having chamber means, said inner tubular member being in telescopically slidable relationship within said outer tubular member;
   needle support means at a first end said inner tubular member for attaching a needle assembly;
   plunger means mounted to a second opposite end of said inner tubular member, said plunger means being axially movable within said inner tubular member;
   resilient means for biasing said outer tubular member to an extended position whereby said needle assembly is enclosed within said outer tubular member;
   latching means on said outer tubular member cooperating with retaining means on said inner tubular member for both securing said outer tubular member in said extended position and for retaining said outer tubular member in a retracted position to expose said needle assembly, said latching means includes first lug means for engaging a first keeper adjacent the first end of said inner tubular member and second lug means for engaging the second end of said inner tubular member.

17. The hypodermic syringe of claim 16 wherein said latching means includes lever means with said first lug means at a first end thereof for latching engagement with a first keeper means on said inner tubular member whereby axial movement between said inner and outer tubular members is prevented when said outer tubular member is in said extended position, said lever means further including said second lug means at a second opposite end of said lever means to engage a second keeper on said inner tubular member to retain said outer member in said retracted position whereby said needle assembly is exposed.

* * * * *